(12) United States Patent
Kashinath

(10) Patent No.: US 11,449,747 B2
(45) Date of Patent: Sep. 20, 2022

(54) ALGORITHM FOR COST EFFECTIVE THERMODYNAMIC FLUID PROPERTY PREDICTIONS USING MACHINE-LEARNING BASED MODELS

(71) Applicant: Saudi Arabian Oil Company, Dhahran (SA)

(72) Inventor: Abishek Kashinath, Cambridge, MA (US)

(73) Assignee: Saudi Arabian Oil Company, Dhahran (SA)

( * ) Notice: Subject to any disclaimer, the term of this patent is extended or adjusted under 35 U.S.C. 154(b) by 1018 days.

(21) Appl. No.: 16/142,757

(22) Filed: Sep. 26, 2018

(65) Prior Publication Data

US 2019/0095792 A1 Mar. 28, 2019

Related U.S. Application Data

(60) Provisional application No. 62/563,460, filed on Sep. 26, 2017.

(51) Int. Cl.
*G06N 3/08* (2006.01)
*G06N 20/10* (2019.01)
*G06N 7/00* (2006.01)
*G06N 20/20* (2019.01)
*G16C 20/30* (2019.01)
*G16C 20/70* (2019.01)
*G06F 30/20* (2020.01)

(52) U.S. Cl.
CPC ............... *G06N 3/08* (2013.01); *G06N 7/005* (2013.01); *G06N 20/10* (2019.01); *G06N 20/20* (2019.01); *G16C 20/30* (2019.02); *G16C 20/70* (2019.02); *G06F 30/20* (2020.01)

(58) Field of Classification Search
CPC ............ G06N 3/08; G06N 3/04; G06N 3/063; G06N 3/082; G06N 20/00
USPC .......................................................... 706/25
See application file for complete search history.

(56) References Cited

U.S. PATENT DOCUMENTS

| 2005/0049990 A1* | 3/2005 | Milenova ............. G06K 9/6253 706/48 |
| 2006/0025975 A1 | 2/2006 | Rey-Fabret et al. |
| 2013/0118736 A1 | 5/2013 | Usadi et al. |

FOREIGN PATENT DOCUMENTS

| WO | 200118667 | 3/2001 |
| WO | 2013135639 | 9/2013 |
| WO | 2018117890 | 6/2018 |

OTHER PUBLICATIONS

Gulf Cooperation Council Examination Report issued in GCC Application No. GC 2018-36070 dated May 25, 2020, 5 pages.

(Continued)

*Primary Examiner* — Viker A Lamardo
(74) *Attorney, Agent, or Firm* — Fish & Richardson P.C.

(57) ABSTRACT

A method for determining isothermal phase behavior for reservoir simulation includes generating a training data set using negative flash calculations, training a first machine learning algorithm to identify a supercritical phase and a subcritical phase, training a second machine learning algorithm to identify a number of stable phases in the subcritical phase, and training a third machine learning algorithm to determine a phase split of the subcritical phase that has more than one identified stable phase.

17 Claims, 6 Drawing Sheets

(56) References Cited

OTHER PUBLICATIONS

Xu et al., "Classification Performance Comparison between RVM and SVM," IEEE International Workshop on Anti-Counterfeiting, Security Identification, 2007, Apr. 1, 2007, 4 pages.

International Search Report and Written Opinion issued in International Application No. PCT/US2018/051684 dated Dec. 12, 2018, 16 pages.

Gaganis and Varotsis, "An integrated approach for rapid phase behavior calculations in compositional modeling," Journal of Petroleum Science and engineering, vol. 118, Apr. 2014.

Gaganis and Varotsis, "Machine Learning Methods to Speed up Compositional Reservoir Simulation," in SPE EUROPEC/EAGE Annual Conference and Exhibition, Society of Petroleum Engineers, SPE 154505, Jun. 2012, 11 pages.

Haugen and Beckner, "Highly Optimized Phase Equilibrium Calculations," in SPE Reservoir Simulation Symposium, Society of Petroleum Engineers, SPE 163583, Feb. 2013, 9 pages.

Kashinath and Szulczewski, "A fast algorithm for calculating isothermal phase behavior using machine learning," Aug. 16, 2018, 32 pages.

Schmitz et al., "Artificial neural networks for the solution of the phase stability problem," Fluid Phase Equilibria, vol. 245, issue 83, Jul. 2006, 5 pages.

GCC Examination Report in Gulf Cooperation Council Appln. No. GC 2018-36070, dated Apr. 30, 2021, 4 pages.

\* cited by examiner

ALGORITHM FOR COST EFFECTIVE THERMODYNAMIC FLUID PROPERTY PREDICTIONS USING MACHINE-LEARNING BASED MODELS

TECHNICAL FIELD

This application claims the benefit of priority to U.S. patent application Ser. No. 62/563,460, filed on Sep. 26, 2017, the contents of which are hereby incorporated by reference.

This disclosure relates to reservoir simulation, and more particularly to identifying isothermal phase behavior for reservoir simulation.

BACKGROUND

In petroleum reservoir simulation, the composition of the reservoir fluids can be described using different models. In a black oil model, petroleum can be modeled as including one oil and one gas component. These components can be pseudo-components, in that they may not refer to any specific chemical components, such as methane or octane, but refer to a collection of components that can exhibit similar phase behavior. In compositional reservoir models, reservoir fluids can be described as a mixture of several pure chemical components, such as carbon dioxide ($CO_2$), hydrogen sulphide ($H_2S$), low-carbon alkanes (for example, methane and ethane), and pseudo-components for heavier hydrocarbons.

Compositional fluid models are increasingly used to simulate production from conventional reservoirs and fields developed using enhanced oil recovery techniques (EOR) (for example, surfactant flooding, polymer flooding, and miscible gas injection), since such models can be more accurate than traditionally used black oil models. In compositional models, reservoir fluid behavior can be generally modeled using an equation of state (EOS) and phase equilibrium calculations that require solving nonlinear systems of equations. These types of equations can be solved for phase stability analysis to determine the number of stable phases at equilibrium for a given composition, temperature, and pressure. If the stability analysis predicts that more than one phase is present, a nonlinear system of equations may also be solved in a phase-split (or flash) calculation to determine the mole fraction of all the phases present and the molar composition of each phase. Both stability and flash calculations may be performed once in every simulation cell at every time step. Therefore, the calculations can account for a major fraction of the total simulation time for up to 70%. As the spatial and temporal resolution of reservoir simulations increases, the computational costs associated with determining the phase behavior may also increase.

SUMMARY

The present disclosure describes isothermal phase behavior identification for reservoir simulation.

In an implementation, a training data set using negative flash calculations is generated. A first machine learning algorithm to identify a supercritical phase and a subcritical phase, a second machine learning algorithm to identify a number of stable phases in the subcritical phase, and a third machine learning algorithm to determine a phase split of the subcritical phase that has more than one identified stable phase are trained.

The previously described implementation is implementable using a computer-implemented method; a non-transitory, computer-readable medium storing computer-readable instructions to perform the computer-implemented method; and a computer-implemented system comprising a computer memory interoperably coupled with a hardware processor configured to perform the computer-implemented method/the instructions stored on the non-transitory, computer-readable medium.

The subject matter described in this specification can be implemented in particular implementations, so as to realize one or more of the following advantages. First, the machine learning algorithm can reduce computation time for phase equilibrium calculations, which in turn, can reduce the overall run time of a compositional reservoir simulation. As such, more simulations can be performed in a fixed time frame, or the computational savings can be used to include more components in a fluid model or include more cells in a geologic model.

Second, the reduced computation time can be beneficial in simulating reservoirs that contain fluids near the critical boundary. These reservoirs often include gas-condensate reservoirs, volatile oil reservoirs, and reservoirs injected with supercritical $CO_2$ for EOR. The machine-learning-based algorithm uses a relevance vector machine (RVM) model to determine whether a fluid mixture is supercritical or not, which can avoid performing a large amount of iterations to make the simulation run faster.

Third, by using models trained using RVMs, the desired speedup by using the machine learning algorithm can be selected based on an error tolerance. Since the RVM models provide both a prediction of the fluid phase (for example, whether the fluid is supercritical or not) and a confidence estimate, the machine learning algorithm can allow the prediction to be supplanted by a negative flash calculation if the confidence estimate falls below a threshold. By decreasing the threshold, lower-confidence predictions may be accepted and the accuracy of the algorithm may decrease while the speedup may increase. For example, accepting an error of approximately 5%, the algorithm can provide a speed-up of greater than 90%.

Other advantages will be apparent to those of ordinary skill in the art.

The details of one or more implementations of the invention are set forth in the accompanying drawings and the description below. Other features, objects, and advantages of the invention will be apparent from the description and drawings, and from the claims.

DESCRIPTION OF DRAWINGS

Like reference numbers and designations in the various drawings indicate like elements.

DETAILED DESCRIPTION

The following description is presented to enable any person skilled in the art to make and use the disclosed subject matter, and is provided in the context of one or more particular implementations. Various modifications to the disclosed implementations will be readily apparent to those skilled in the art, and the general principles defined in the present disclosure may be applied to other implementations and applications, without departing from scope of the disclosure. Thus, the present disclosure is not intended to be limited to the described implementations, but is to be accorded the widest scope consistent with the principles and features disclosed in the present disclosure.

This disclosure generally describes methods and systems, including computer-implemented methods, computer program products, and computer systems, for determining isothermal phase behavior through thermodynamic fluid property predictions in petroleum reservoir simulation. In some implementations, machine learning algorithms (MLAs) can be trained to calculate isothermal phase equilibria and related fluid properties to efficiently build a Jacobian for solving fluid flow equations.

In some implementations, negative flash calculations can be used to generate training data sets including inputs and outputs to train the MLAs. The negative flash calculations can be used to distinguish the super-critical phase state, subcritical single-phase state, and subcritical two-phase states. The inputs and the solutions of the negative flash calculations can be stored as input-output examples to build the training data set to train the MLAs.

The training of the machine learning method can include three high-level steps. First, a MLA can be trained to identify a first classifier used to identify if the input conditions correspond to a supercritical region or a subcritical region. Second, a MLA can be trained to identify a second classifier to identify the number of stable phases in the subcritical region. In some cases, a relevance vector machine (RVM) can be used as the MLA to identify the first classifier and the second classifier. The RVM can determine the posterior probabilities for each class, which can be subsequently used to construct a criterion for accepting the predicted phase state. Third, for the subcritical region with two stable phases (that is, the subcritical two-phase region), the phase split can be determined by training a MLA to predict equilibrium vapor-liquid distribution ratios (K-values) for a given pressure and composition. In some cases, an artificial neural network (ANN) algorithm can be used as the MLA to determine the phase split.

Figure 1A:
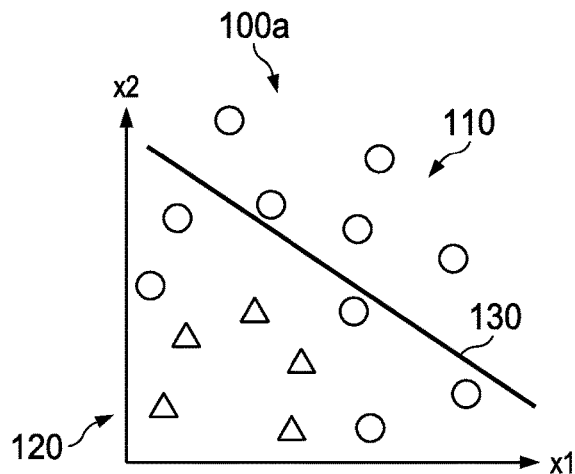
FIG. 1A is a phase diagram showing an example supercritical and subcritical phase-point classification, according to some implementations of the present disclosure.
Figure 1B:
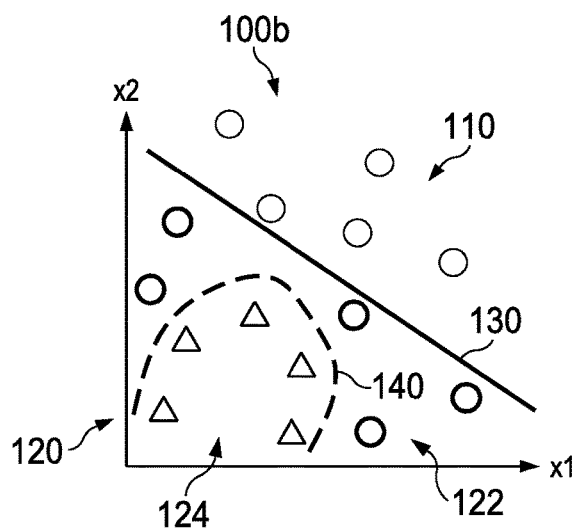
FIG. 1B is a phase diagram showing an example supercritical and subcritical phase-point classification, and single-phase and two-phase subcritical phase-point classification, according to some implementations of the present disclosure.

This machine learning method can eliminate costly iterations in solving the flash problem and reduce the overall run time of phase behavior calculations with little impact on accuracy. The principles of the machine learning method for determining phase equilibrium are further discussed in the examples discussed in the descriptions of FIGS. 1A and 1B. FIG. 1A corresponds to the first training step that identifies a first classifier to classify supercritical region and subcritical region. FIG. 1B corresponds to the second training step that identifies a second classifier to classify single-phase and two-phase subcritical region.

FIG. 1A is a phase diagram showing an example 100*a* supercritical and subcritical phase-point classification, according to some implementations of the present disclosure. In this example 100*a*, two input variables x1 and x2 are used to train a first machine-learning model. The input variables x1 and x2 can represent mole fractions of two components in a feed. The mole fraction can be defined as the amount of a component (expressed in moles) divided by the total amount of all components (expressed in moles) in the feed.

The first MLA is trained to identify a first classifier 130 (shown in FIG. 1A as a boundary line) that can separate each input pair (x1, x2) into a supercritical region 110 (upper right of the boundary line) and a subcritical region 120 (lower left of the boundary line). The first MLA can be algorithms such as support vector machines (SVMs), RVMs, ANNs, and decision trees. The first MLA may be trained by a plurality of input pairs (x1, x2) to identify the first classifier 130. Once the first MLA is optimized, the first classifier is said to be trained and can be used to predict the supercritical and subcritical phase behavior of any input pairs. For example, if an input pair is located in the supercritical region 110, the output of the first classifier is a supercritical phase label.

FIG. 1B is a phase diagram showing an example 100*b* supercritical and subcritical phase-point classification, and a single-phase and two-phase subcritical phase-point classification, according to some implementations of the present disclosure.

A second MLA can be trained to identify a second classifier 140 (shown in FIG. 1A as a boundary curve) that can separate each input pair (x1, x2) in the subcritical region 120 into a single-phase subcritical region 122 (between the boundary line 130 and the boundary curve 140) and a two-phase subcritical region 124 (lower left of the boundary curve 140). Again, the second MLA can be any algorithms such as SVMs, RVMs, ANNs, and decision trees. As described earlier, in some implementations, RVMs can be used as the first MLA and the second MLA, because not only can it identify the classifier, but it can also determine how accurate the classification is. After training the first and second MLAs, both the first classifier 130 and the second classifier 140 are optimized to determine whether an input pair is a supercritical, single-phase subcritical, or two-phase subcritical phase point. The training of the MLAs for identifying the first classifier 130 and the second classifier 140 can use the results of negative flash calculations.

When an input pair is in the two-phase subcritical region 124, more information about how much of each phase is present and what the composition of each phase is can be identified using a third MLA. In other words, the third MLA is used to make quantitative predictions about the phase composition and the amount of each phase. For example, the fraction of phase 1 can be expressed as a regression function of the input pairs (x1, x2), such that for any input pair, the fraction of phase 1 can be determined based on the regression function. The third MLA can be used to identify the form of the regression function through optimization. The third MLA can be any machine learning based regression model, such as ANNs, SVMs, RVMs, Decision forest regression, and Boosted regression tree regression. In some implementations, an ANN can be used as the third MLA since it is accurate once trained and has low computational complexity. The machine learning based regression algorithms can identify the regression function that predicts the fraction of phase for a given input pair (x1, x2). The regression function can then be used to predict the fraction of phase 1 for any input pair during reservoir simulation.

The trainings for the first, second, and third MLAs are performed before the start of the reservoir simulation. After the reservoir simulation starts, the first classifier 130, the second classifier 140, and the regression function can be used to calculate the phase behavior for each reservoir cell.

Figure 2:
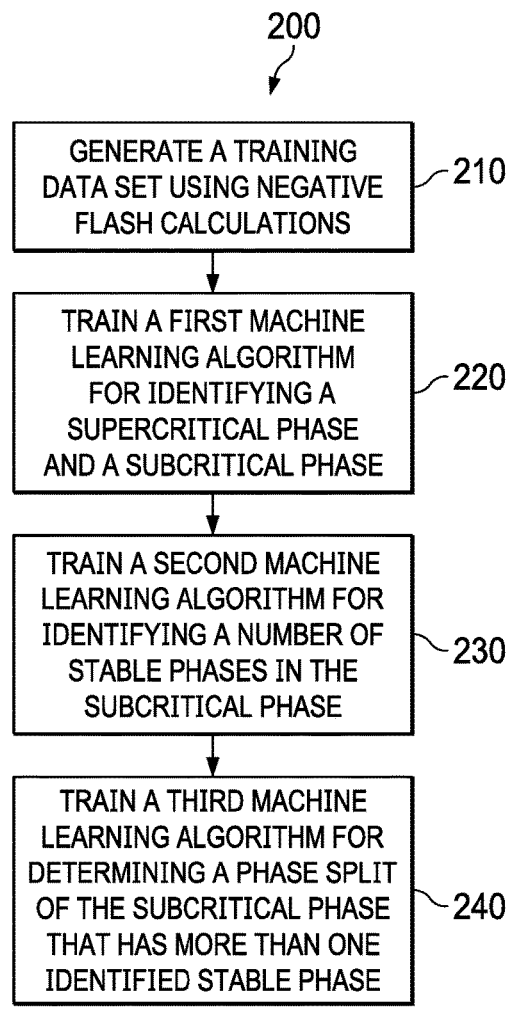
FIG. 2 is a flow chart showing an example machine learning method for determining phase equilibrium determination, according to some implementations of the present disclosure.

FIG. 2 is a flowchart showing an example machine learning method 200 for determining phase equilibrium determination. For clarity of presentation, the description that follows generally describes method 200 in the context of the other figures in this description. However, it will be understood that method 200 can be performed, for example, by any suitable system, environment, software, and hardware, or a combination of systems, environments, software, and hardware, as appropriate. In some implementations, various steps of method 200 can be run in parallel, in combination, in loops, or in any order. Machine learning techniques are used to model complex relationships between inputs and outputs, if provided with adequate training information. In this example method 200, the inputs are the fluid composition, $\{z_i\}$, and pressure, P, of a simulation cell and the output is the equilibrium phase state, which is the number of stable phases and their compositions. The relationships of interest are the phase boundaries in the corresponding phase diagram. Machine learning techniques are used to generate models that predict phase behavior. At a high-level, a training data set of input-output examples are calculated by solving a negative flash problem over a feed composition and pressure range of interest. MLAs are then trained using the training data set to predict a solution of the phase equilibrium problem.

At 210, training data set is generated using negative flash calculations. The training data set can be generated by solving the two-phase isothermal negative flash problem over the reservoir pressure and composition range. The advantages of this method include: (1) the phase stability and the phase split problems are solved simultaneously, and (2) the negative flash procedure can distinguish between the supercritical and subcritical phase state. The solution to the problem is determined by requiring the fugacity, $f_i^\alpha$, for each component i=1, 2, ..., n in each phase, $\alpha$, of the two-phase mixture to be equal at equilibrium:

$$f_i^L - f_i^V = x_i \varphi_i^L P - y_i \varphi_i^V P = 0$$

$$K_i = \frac{y_i}{x_i} = \frac{\varphi_i^L}{\varphi_i^V}$$

where L and V denote the liquid and vapor phase, $x_i$ and $y_i$ are the mole fractions of component i in the liquid and vapor phase, $\varphi_i^\alpha$ is the fugacity coefficient of component i in the $\alpha$ phase, and $K_i$ is the equilibrium ratio for component i (also called the K-value). The mole balance for each component requires that:

$$z_i = \beta y_i + (1 - \beta) x_i$$

$$x_i = \frac{z_i}{1 + \beta(K_i - 1)}$$

$$y_i = \frac{z_i K_i}{1 + \beta(K_i - 1)}$$

where $\beta$ is the fraction of moles in the vapor phase relative to the total number of moles. Finally, the constraint that the component mole fractions in each phase sum to one is used to derive the Rachford-Rice relationship:

$$\sum_{i=1}^{n} \frac{z_i(K_i - 1)}{1 + \beta(K_i - 1)} = 0$$

The component K-values and $\beta$ can be calculated iteratively, using the successive substitution method. One Rachford-Rice iteration can be defined as an update of $\beta$ at fixed $\{K_i\}$, followed by an update of $\{K_i\}$ with $\beta$ held constant. In some implementations, Wilson's correlation can be used to seed the method with initial estimates for $\{K_i\}$. The procedure converges as long as the feed composition is positive and if $\beta$ is in the range $$\frac{1}{1 - K_{max}} < \beta < \frac{1}{1 - K_{min}}.$$

Convergence to a non-trivial solution ($x_i \neq y_i$) with $\beta \leq 0$ implies that the input conditions correspond to a single-phase liquid at equilibrium, a single-phase vapor when $\beta \geq 1$, and a two-phase mixture when $0 < \beta < 1$. For compositions in the critical region, the method converges to the trivial solution: $x_i = y_i = z_i, \forall i$.

The negative flash calculations can be performed for a large number of inputs ($\{z_i\}$, P). The inputs and the solutions ($\beta$, $\{x_i\}$, $\{y_i\}$) from the negative flash calculations can be stored as input-output examples in order to build the training data set. The input vectors can be drawn randomly from the (n+1)-dimensional space spanned by the range of pressures and compositions the reservoir can exhibit under operating conditions. While the pressure can be freely picked in the operating range, the feed mole fractions can be drawn from a (n−1)-dimensional unit simplex in order to satisfy the constraint that the mole fractions sum to one, which is obtained by following the Bayesian bootstrap method. From 210 example method 200 proceeds to 220.

At 220, a first machine algorithm is trained for identifying a supercritical phase and a subcritical phase. The first task of the algorithm, identifying the presence of a supercritical phase, can be treated as a classification problem. This is based on the observation that the negative flash converges to the trivial solution, $x_i = y_i = z_i$, and that the length of the tie-line, t, is zero for any point in the supercritical region. The length of the tie-line can be defined as:

$$t = \sqrt{\sum_{i=1}^{n}(x_i - y_i)^2}$$

On the other hand, the tie-line length is greater than zero for any hydrocarbon mixture in the subcritical region irrespective of the number of stable phases present at equilibrium. Based on this observation, the length of the tie-line can be used to recast the supercritical phase detection problem as a binary classification problem with the following rule:

$$\text{Phase state is} \begin{cases} \text{supercritical,} & \text{if } t = 0 \\ \text{sub-critical,} & \text{if } t > 0 \end{cases}$$

In some implementations, the classification problem can be solved based on discriminant functions generated by training SVMs. For any input, the discriminant function is evaluated to assign the label without considering the confidence level of the prediction. Instead, the classification problem is split into two steps—the inference step of training the model and a decision step using the posterior probability of the predicted label and a threshold value for acceptance. The advantage of this method over discriminant functions is that the misclassification rate can be reduced by rejecting predictions with a probability less than the discriminant threshold value, $\theta_1$. RVMs can be used to fit the decision boundary that separates the subcritical and supercritical regions in phase space. The output of the RVM is the class label, SC, and the probability that the predicted label is correct, P(SC). SC=1 corresponds to the supercritical phase state and SC=0 denotes the subcritical phase. If P(SC) is greater than $\theta_1$, the answer of the RVM is accepted and rejected otherwise. The confidence estimate of the trained model is improved by increasing the density of training points in the vicinity of the surface separating the two regions. The tie-line length is used to identify subcritical points that are close the boundary since the critical surface corresponds to the surface where t=0. Inputs in the subcritical region are sorted in increasing order of tie-line lengths and points with t greater than a cut-off value are neglected.

At 230, a second MLA is trained for identifying a number of stable phases in the subcritical phase. Similarly, identifying the number of stable phases at equilibrium can also be re-formulated as a multi-class classification problem, solved by training another RVM model. First, training data set is pruned by removing points belonging to the supercritical region. For points in the subcritical region, the phase label is assigned using β from the negative flash solution as follows:

$$\text{Phase is} \begin{cases} \text{single-phase liquid,} & \text{if } \beta \leq 0 \\ \text{two-phase mixture,} & \text{if } 0 < \beta < 1 \\ \text{single-phase vapor,} & \text{if } \beta \geq 1 \end{cases}$$

After training, the RVM model can represent an approximation for the bubble point curve (β=0) and the dew point curve (β=1). Therefore, models with better predictive capability are generated by selecting training points that lie in the vicinity of the two curves, as measured by the value of β. The output of the trained model is the class label, #ph={0, 1,2}, and its likelihood value, P(#ph). Here, #ph=0 denotes a single-phase vapor, #ph=1 denotes a single-phase liquid, and #ph=2 denotes a two-phase mixture. P(#ph) is used to implement a rejection criterion by comparing it against a discriminant threshold value, $\theta_2$, and neglecting answers with P(#ph) less than that threshold.

At 240, a third MLA is trained for determining a phase split of the subcritical phase that has more than one identified stable phase. The third step of solving the phase equilibrium problem is to determine the compositions of the liquid and vapor phases in a two-phase mixture by solving the equal fugacity constraint and Rachford-Rice equation simultaneously for $\{K_i\}$ and β. This step is accelerated by generating initial K-value estimates using a function that is tailored for the phase diagram under consideration as opposed to using an empirical relationship such as Wilson's correlation. The acceleration can be attributed to the fact that the predicted $\{K_i\}$ can either satisfy the equal fugacity constraint to within some tolerance, δ, eliminating Rachford-Rice iterations or provide an accurate guess that reduces the number of iterations for convergence.

In some implementations, nonlinear regression can be used to obtain more accurate initial K-value estimates. Nonlinear regression can be used to fit a function, g, to predict $\{K_i\}$ for a given pressure and composition by optimizing its parameters, w, to match the EOS-based solution:

$$\{K_i\} = g(\{z_i\}, P, w)$$

In some implementations, ANN can be used for function regression to eliminate the need for a user-defined function for g. Another advantage of ANNs is that they can capture complex nonlinear relationships with relatively few parameters, enabling cheap computations of g. The function weights, w, are optimized to minimize the mean squared error between the predicted $\{K_i\}$ and the training data set. The $\{z_i\}$ and P corresponding to negative flash solutions in the two phase region can be selected to build the data set for training the ANN. Overfitting is avoided by using early-stopping and minimizing the number of neurons in the hidden layer of the ANN required to produce a satisfactory fit.

Figure 3:
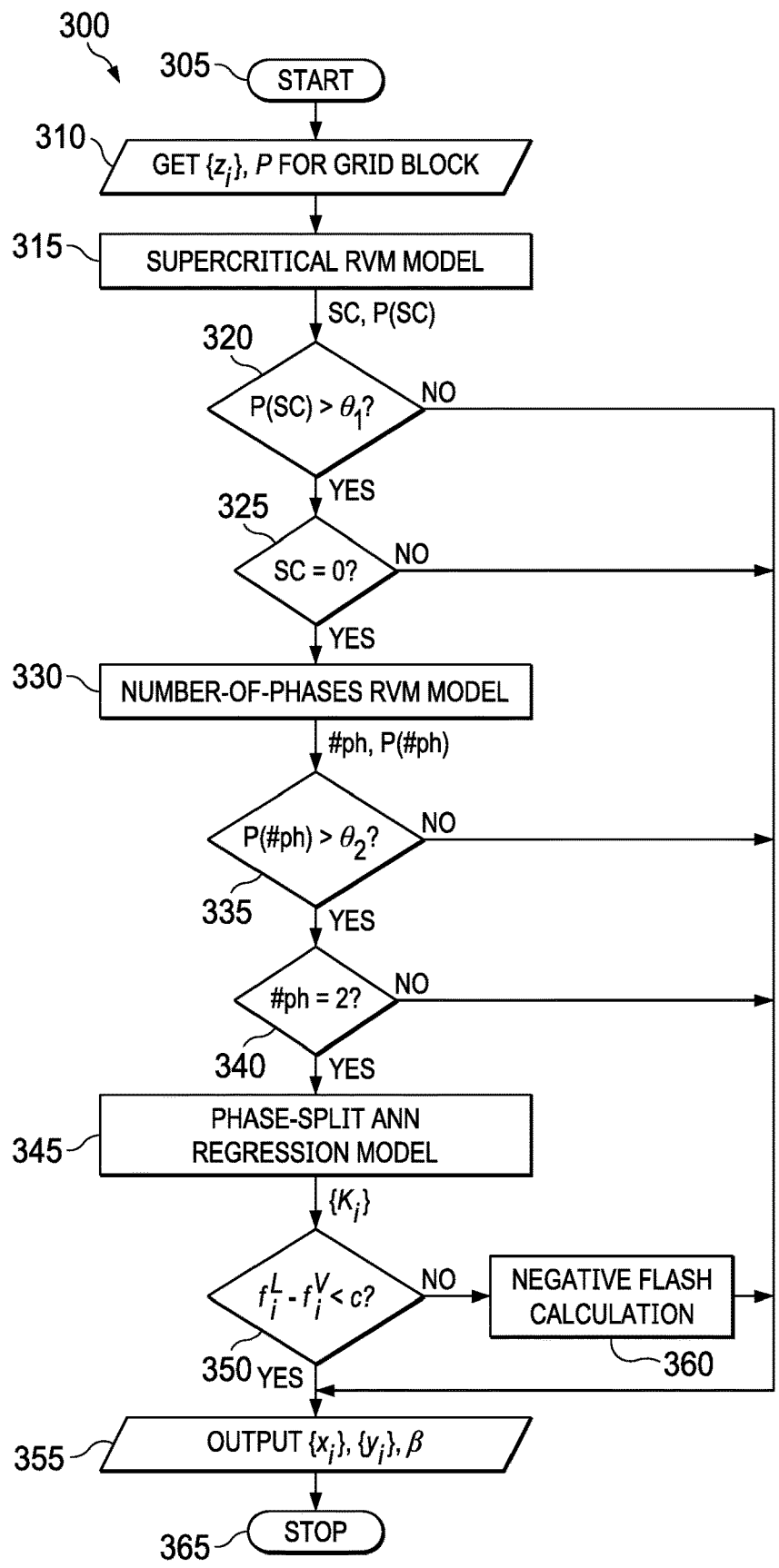
FIG. 3 is a flow chart showing an example algorithm for phase equilibrium calculations based on machine learning methods, according to some implementations of the present disclosure.

FIG. 3 is a flow chart showing an example algorithm 300 for phase equilibrium calculations using the trained machine learning models, according to some implementations of the present disclosure. For clarity of presentation, the description that follows generally describes method 300 in the context of the other figures in this description. However, it will be understood that method 300 can be performed, for example, by any suitable system, environment, software, and hardware, or a combination of systems, environments, software, and hardware, as appropriate. In some implementations, various steps of method 300 can be run in parallel, in combination, in loops, or in any order. The trained models, that is, the supercritical RVM classifier, the number of phases RVM classifier, and the phase split ANN regression model, can be linked together to create a new algorithm for calculating the equilibrium phase state.

At a high-level, the example method uses three MLAs. First, it uses a relevance vector machine (RVM) to determine whether a fluid is supercritical or subcritical. If the fluid is not supercritical, it uses another RVM to determine if it is a liquid, a vapor, or a two-phase fluid. For a two-phase fluid, it uses an artificial neural network (ANN) to determine the phase split.

The example algorithm 300 starts at 305.

At 310, the simulation cell is queried for the feed composition, $\{z_i\}$, and pressure, P.

At 315, the supercritical RVM model is evaluated to obtain the class label, SC, and the corresponding probability value, P(SC).

At 320, whether P(SC) is greater than the discrimination threshold value, $\theta_1$ is determined. If P(SC)>$\theta_1$, then the class label is accepted as the true solution, and the algorithm 320 proceeds to 325. Otherwise, the RVM response is rejected and the algorithm 300 proceeds to 360, where the negative flash method is used to determine the phase state.

At 325, the value of SC is determined. If SC=0, the phase state detected is subcritical and the algorithm 300 proceeds 330 where it determines the number of stable phases at equilibrium. If SC=1, the algorithm 300 proceeds to 355, where a supercritical phase is detected, the solution ($\{x_i\}=\{y_i\}=\{z_i\}$, $\beta=0$) is output, and the algorithm then stops at 365.

At 330, the RVM classifier is evaluated to determine the number of stable phases, #ph, and its probability, P(#ph).

At 335, whether P(#ph) is greater than the acceptance threshold, $\theta_2$ is determined. If P(#ph)>$\theta_2$, the RVM response is accepted and the algorithm 300 proceeds to 340. Otherwise, the answer is rejected and the process proceeds to 360 where the inputs are forwarded to the negative flash calculations.

At 340, the value of #ph is determined. If #ph=0, the equilibrium phase corresponds to a single-phase vapor state ($\{x_i\}=0$, $\{y_i\}=\{z_i\}$, $\beta=1$). If #ph=1, the equilibrium phase corresponds to a single-phase liquid state ($\{x_i\}=\{z_i\}$, $\{y_i\}=0$, $\beta=0$), and the algorithm 300 proceeds to 355. If #ph=2, the equilibrium phase corresponds to a two-phase state. A phase split calculation can be performed to determine $\{x_i\}$, $\{y_i\}$, and $\beta$, and the algorithm proceeds to 345.

At 345, the phase split is calculated by running a phase-split ANN regression model. The K-values ($\{K_i\}$) are calculated by evaluating the trained phase split regression model.

At 350, the fugacity for each component is checked. If the fugacities of all components in both phases are equal to within some error tolerance, $\delta$, the Rachford-Rice equation is solved once to calculate $\{x_i\}$, $\{y_i\}$, and $\beta$, and algorithm 300 stops at 365. If the component fugacities are not equal, the predicted $\{K_i\}$ is used as an initial guess for the negative flash method at 360 and the algorithm stops at 365 after a solution is obtained.

The results of the algorithm can be compared with the negative flash results for the same inputs to determine the accuracy and computational speedup. The error may arise from two sources: misclassification rate of the RVMs and the average absolute relative error (AARE) in the vapor fraction as a result of not satisfying the equal fugacity constraint in the two-phase region. The misclassification rate can be defined as:

$$\text{Misclassification rate} = \frac{1}{m}\sum_{j=1}^{m}[Y_j \neq \hat{Y}_j]$$

where [ . . . ] represents the Iverson bracket, m is the total number of examples, $Y_j$ is the class label predicted by the RVM for the $j^{th}$ example, and $\hat{Y}_j$ is the class label calculated using the negative flash method. The AARE in the vapor fraction is calculated as follows:

$$AARE = \frac{1}{m}\sum_{j=1}^{m}\left|\frac{\beta_j - \hat{\beta}_j}{\hat{\beta}_j}\right|$$

where $\beta_j$ is the vapor fraction predicted by the algorithm for the $j^{th}$ instance and $\hat{\beta}_j$ is the vapor fraction corresponding to the negative flash solution. The speedup can be measured as the difference in the mean number of Rachford-Rice iterations required for convergence in the algorithm and the negative flash method. This measure does not include the computational cost of evaluating the trained models but the additional cost incurred can be small relative to the cost of a Rachford-Rice iteration and will not change the results. The speedup and accuracy of the algorithm can be tailored by selecting $\theta_1$, $\theta_2$, and $\delta$. Setting loose tolerances will produce a fast but approximate answer and vice versa.

The algorithm for rapid phase behavior determination can be tested using three different reservoir fluid mixtures of increasing complexity: three, six, and thirteen component mixtures. In all cases, the ranges of pressure and composition for which the phase diagram includes supercritical and subcritical regions are considered.

Figure 4A:
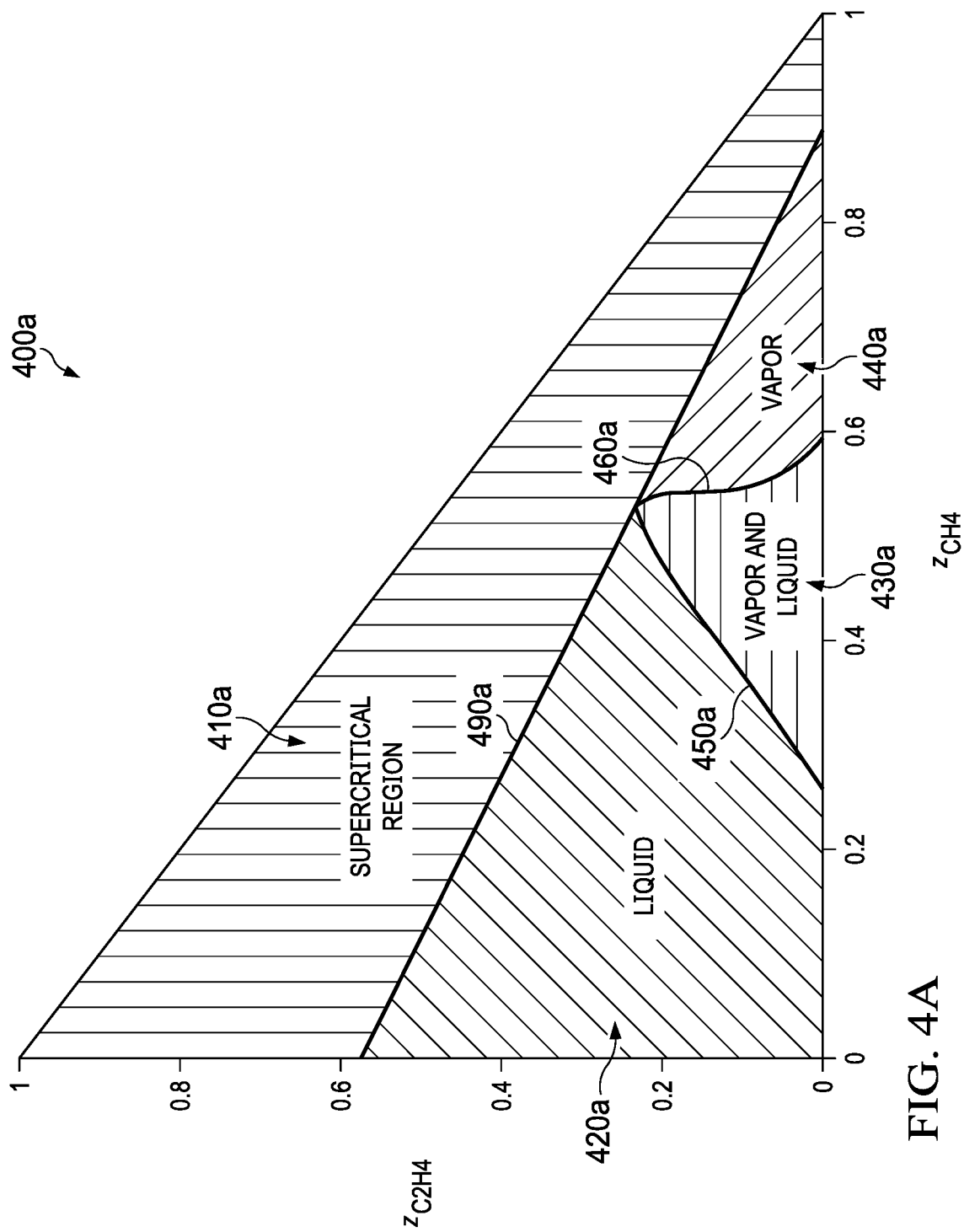
FIG. 4A is a phase diagram showing an example phase behavior of a hydrocarbon mixture at a given temperature and pressure, according to some implementations of the present disclosure.

FIG. 4A is a phase diagram 400a showing an example phase behavior of a hydrocarbon mixture at a given temperature and pressure, according to some implementations of the present disclosure. In this example, the phase diagram is for a $CH_4$—$C2H_6$—$CO_2$ ternary system at 260 Kelvin (K) and 7 megaPascal (MPa). The phase behavior of the $CH_4$—$C2H_6$—$CO_2$ mixture is generated using negative flash calculations with respect to the mole fractions of $C_2H_6$ and $CH_4$ at 260 K and 7 MPa. The phase diagram 400a shows a critical surface 490a separating the supercritical region 410a and subcritical regions. The subcritical regions include a liquid region 420a, a vapor and liquid mixture region 430a, and a vapor region 440a. The phase diagram 400a also shows the bubble-point curve 450a and dew-point curve 460a that bound the two-phase region.

Figure 4B:
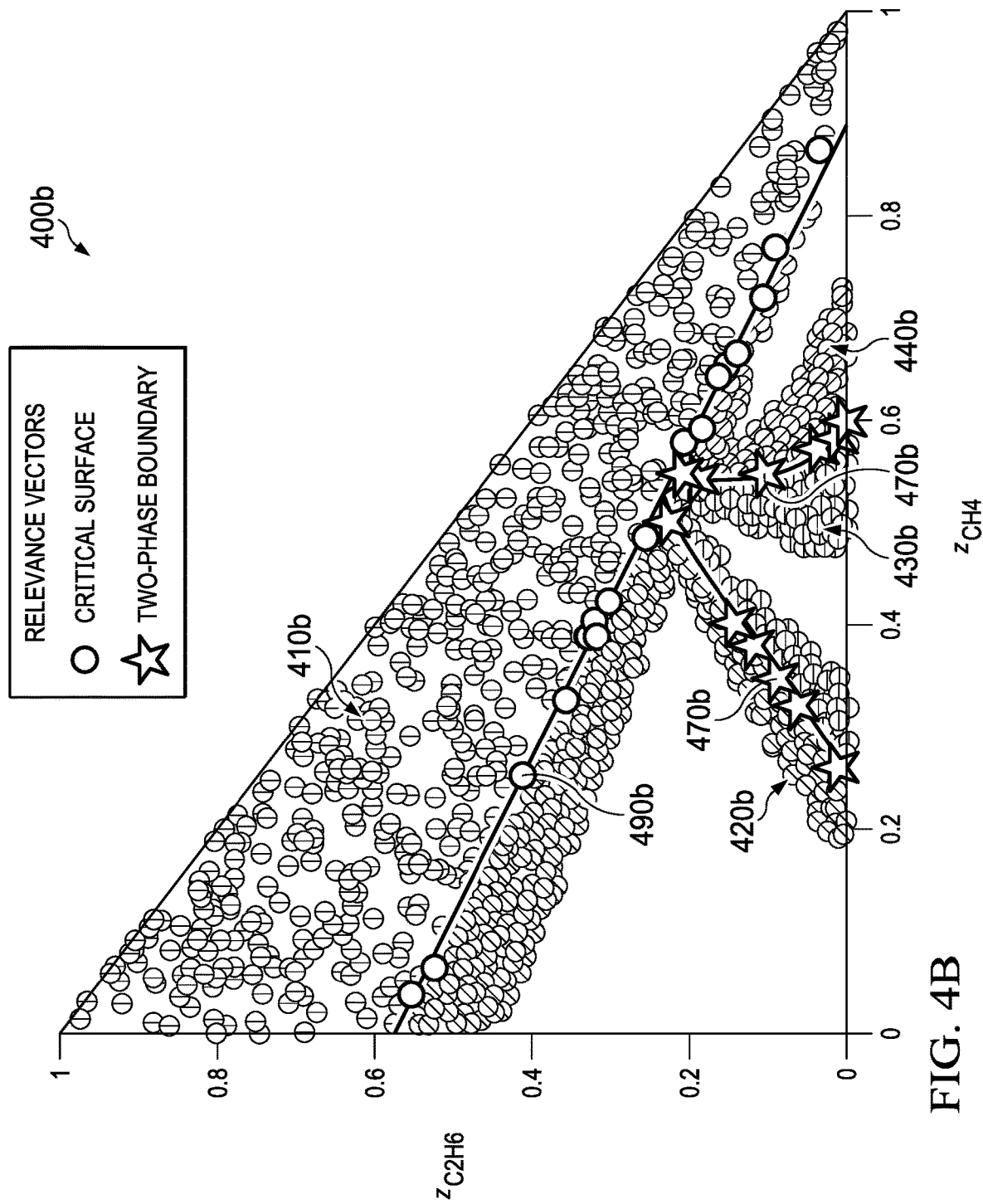
FIG. 4B is a phase diagram showing examples of models trained using machine learning methods to classify the phase behavior of a hydrocarbon mixture at a given temperature and pressure into supercritical, sub-critical single phase, and sub-critical two-phase regions, according to some implementations of the present disclosure.

FIG. 4B is a phase diagram 400b showing another example phase behavior of a hydrocarbon mixture at a given temperature and pressure along with two machine-learning models trained to classify the supercritical phase, the sub-critical liquid phase, the sub-critical vapor phase, and sub-critical two-phase region, according to some implementations of the present disclosure. A data set for this phase diagram is calculated using the negative flash method, and the data set is used to train two RVMs. One RVM model classifies the input fluid as either supercritical 410b or subcritical. For this model, relevance vectors are shown as open circles 490b. Another RVM model classifies the fluid as a liquid 420b, a vapor 440b, or a two-phase mixture 430b. For this model, relevance vectors lie on the two-phase boundary and are shown as open stars 470b.

For each of the three cases, the phase diagram data are used to train the three machine-learning models. The trained RVM models can predict the critical behavior and number of stable phases at equilibrium with an accuracy greater than 98.9% even when $\theta_1$ and $\theta_2$ are set to the lowest value of 0.5. The RVM models for predicting the critical phase and number of stable phases for the three component mixture at 260 K and 7 MPa are illustrated in FIG. 4B. The figure shows that the first RVM model separates the supercritical and subcritical regions using relevance vectors that lie on the critical surface. Similarly, the second RVM model identifies the single-phase liquid, single-phase vapor, and two-phase regions using relevance vectors to represent the two-phase boundary. The ANN regression models use 25 to 50 neurons in the hidden layer to predict $\{K_i\}$ to within $10^{-4}$ of the value calculated from the EOS-based model across the fluid mixtures of interest.

The trained models are subsequently integrated in the algorithm and tested using $5\times10^5$ input-output examples. The number of Rachford-Rice iterations and the phase equilibrium solution predicted by the method are compared with the negative flash solution to measure the speedup and accuracy. Furthermore, the comparison is carried out at different values of $\theta_1$, $\theta_2$, and ò to investigate the effect of these parameters on the total error and computational cost of phase behavior calculations. The results of the study are illustrated in FIG. 5.

Figure 5:
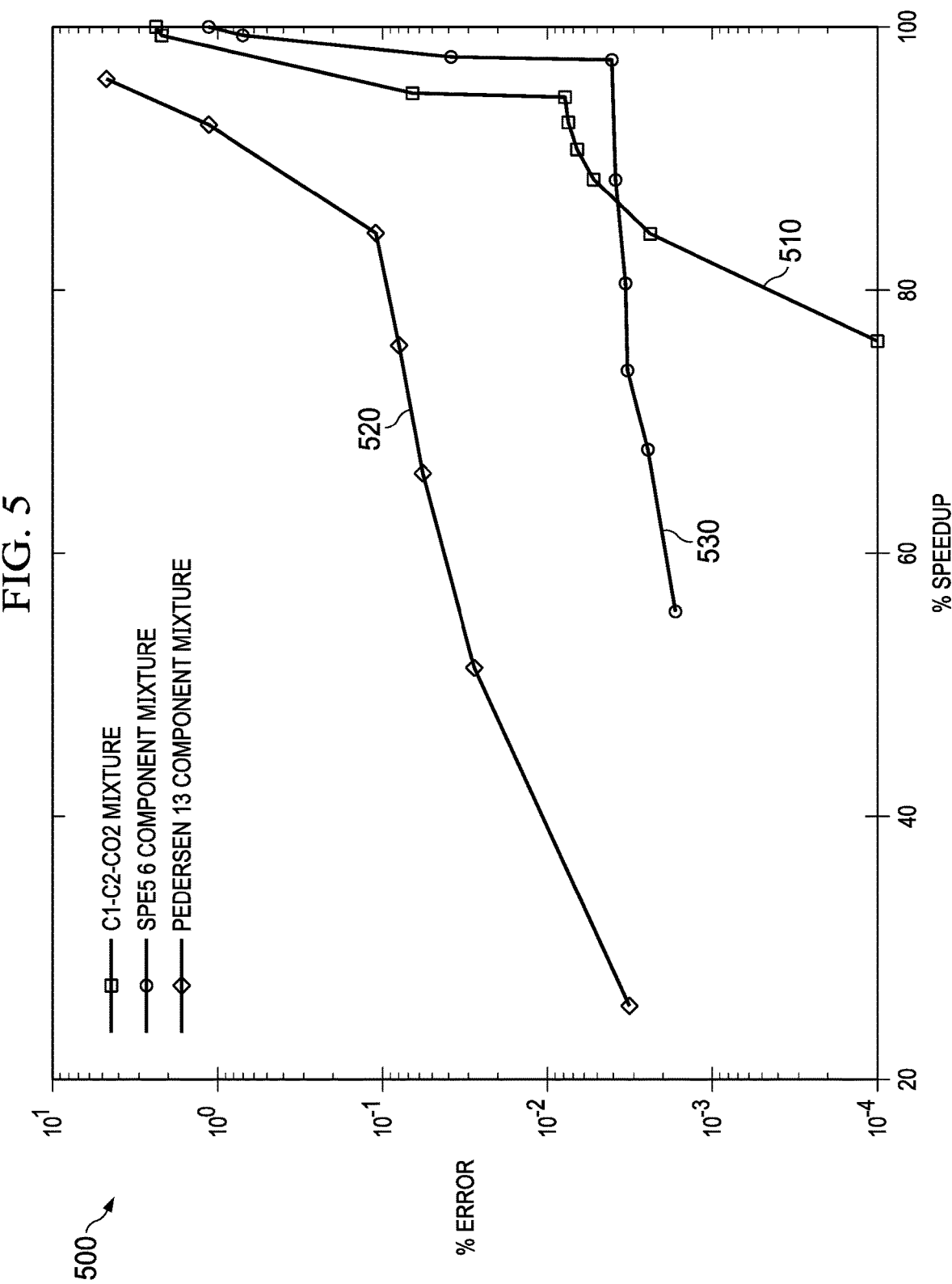
FIG. 5 is a diagram showing example misclassification error and average absolute relative error with respect to a speed gain using a rapid flash algorithm, according to some implementations of the present disclosure.

FIG. 5 is a diagram showing example 500 misclassification error and average absolute relative error with respect to a speed gain using a rapid flash algorithm, according to some implementations of the present disclosure. The error is the sum of the misclassification error and the average absolute relative error (AARE) in the vapor fraction of two-phase results. The speedup is defined as the relative decrease in the number of Rachford-Rice iterations between the algorithm and conventional negative flash. The algorithm offers a speed gain of greater than 90% with a maximum error of 5% across all the cases. As shown in FIG. 5, the algorithm can reduce the computational cost of phase equilibrium calculations by over 20% with an error on the order of $10^{-3}$ relative to the EOS solution. The speedup varies between 25% for the thirteen-component model to 76% for the three-component case when $\theta_1\theta_2=0.995$ and ò$=10^{-5}$. The algorithm is faster than conventional phase equilibrium calculations due to the fact that expensive iterative calculations are replaced by computationally cheap function evaluations of the machine-learning models. When the values of $\theta_1$ and $\theta_2$ are relaxed to 0.5 and the value of ò is relaxed to $10^{-2}$, the measured speedup increases to over 95% but the maximum error also increases to 4.6%. The total error increases because both the misclassification rate and AARE in the vapor fraction increase. The misclassification rate increases because lower confidence labels are accepted as the correct answer. When ò is increased, the equal fugacity constraint is not satisfied, and the AARE in the vapor fraction increases because the phase-split problem is not solved until a converged solution is obtained.

The machine-learning-based algorithm for equilibrium phase determination offers several advantages over the negative flash method alone. One of the main advantages is the reduction in computation time. This reduction can decrease the overall run time of a compositional reservoir simulation, which would provide reservoir simulation engineers with several benefits: they can complete more simulations in a fixed time frame, or use the computational savings to include more components in the fluid model or more cells in the geologic model.

The reduced computation time can be particularly advantageous in simulating reservoirs that contain fluids near the critical boundary. These reservoirs often include gas-condensate reservoirs, volatile oil reservoirs, and reservoirs injected with supercritical $CO_2$ for EOR. The negative flash method requires a large number of iterations for fluids near the critical boundary when compared to systems that are far away from the critical boundary. Since the machine-learning-based algorithm uses a RVM model to determine whether a fluid mixture is supercritical or not, these iterations can be avoided and the simulation may run faster.

Another advantage of the machine-learning-based algorithm is that the desired speedup can be chosen according to one's error tolerance. This capability derives from the use of RVMs. Since our RVM models provide both a prediction of the fluid phase (for example, the fluid is supercritical or not) and a confidence estimate, our algorithm allows the prediction to be supplanted by a negative flash calculation if the confidence estimate is less than a threshold. By decreasing the threshold, lower-confidence predictions are accepted and the accuracy of the algorithm decreases, but the speedup increases.

This trade-off curves are plotted for three fluid samples in FIG. 5, including C1-C2-$CO_2$ mixture trade-off curve 510, Pedersen 13 component mixture trade-off curve 520, and SPE5 6 component mixture trade-off curve 530. These types of plots can be used by reservoir simulation engineers to set the desired accuracy for a given run time. If an engineer chooses to accept an error of less than 0.01%, our results suggest that the algorithm would still provide a speed-up of greater than 20%. This ability to reject low-confidence solutions and thereby trade accuracy for run time is not possible using SVMs.

Compared to other methods to speed up phase equilibrium calculations, the machine-learning-based algorithm is extensible. The method can be extended to EOS other than Peng-Robinson (PR) or Soave-Redlich-Kong (SRK), including non-cubic EOS such as perturbed-chain statistical association fluid theory (PC-SAFT) and cubic-plus-association (CPA), without sacrificing speed since it depends on phase behavior calculations only for the training stage. Non-cubic EOS can be more accurate than cubic EOS, but are less used in reservoir simulation since the phase behavior calculations for non-cubic EOS can be three times as expensive as those for cubic EOS. In contrast, reduction methods, which exploit the sparsity of the binary interaction parameter (BIP) matrix, cannot be easily extended to mixtures modeled using a non-cubic EOS. While offering extensibility to different EOS, the algorithm can also be extended to problems with more than two stable phases. Multi-class classification can be used to assign labels to each region of phase space, similar to how different labels are assigned for a single-phase vapor, a single-phase liquid, and a two-phase mixture.

The machine-learning-based algorithm also requires low data storage and is not sensitive to changes in the fluid composition of a grid cell over time, when compared to other methods. The algorithm requires less data storage than methods such as compositional space parameterization (CSP), compositional space tabulation (CST), and compositional space adaptive tabulation (CSAT), which store and search tie-line lists. As these lists become larger, the speed of these methods also decreases. Finally, the speed of the algorithm is not affected by how the fluid composition in a grid cell changes over time. In contrast, methods that use the phase equilibrium solution from the previous time step will provide a smaller speed up if that solution does not accurately approximate the current solution. This feature of the algorithm can be important for reservoir simulations with billions of simulation cells. In such high-resolution simulations, the numerical dissipation can be less than in lower resolution simulations and, as a result, the fluid composition in a grid cell may exhibit larger changes between time steps.

In addition to benefiting reservoir simulators, the machine-learning-based algorithm could benefit other applications in the oil industry. It could reduce the simulation time of processes that require determining the phase equilibrium, such as the separation of production fluids in surface facilities, the flow of hydrocarbons in pipelines, and the distillation of crude oil.

While this method offers several advantages when compared to other rapid flash techniques, it also has several disadvantages. Firstly, the application of this technique in reservoir simulators affects the process workflow since machine-learning-based models need to be trained in addition to optimizing the parameters of the EOS model. Secondly, it is not possible to automate the training procedure since the choice of the MLA is critical to obtaining an accurate model. However, this process is heuristic and several machine learning methods need to be investigated in order to identify the model with the highest accuracy. Further work is required to study the effectiveness of different machine learning methods for each stage of the algorithm. The results of such a study can be used to automate the fitting process and generate the trained models as inputs for the reservoir simulator. Another disadvantage of this method is that the models are applicable only over the pressure range used in the training stage. If the pressure exceeds these bounds, the method may not provide any speedup. In such cases, a conventional phase calculation can be used for pressures outside the training range or, if deemed necessary, the models can be re-trained over the phase diagram corresponding to the extended pressure range.

Figure 6:
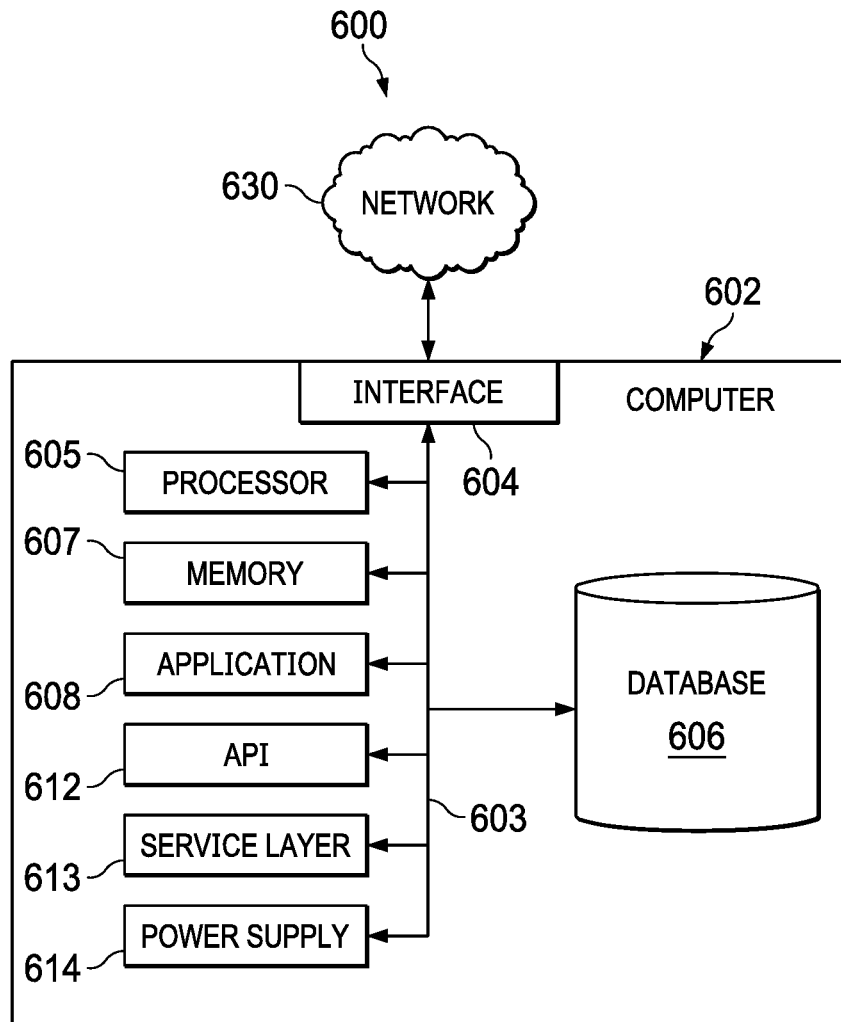
FIG. 6 is a block diagram illustrating an example computer system used to provide computational functionalities associated with described algorithms, methods, functions, processes, flows, and procedures as described in the instant disclosure, according to some implementations of the present disclosure.

FIG. 6 is a block diagram of an example computer system 600 used to provide computational functionalities associated with described algorithms, methods, functions, processes, flows, and procedures, as described in the instant disclosure. The illustrated computer 602 is intended to encompass any computing device such as a server, desktop computer, laptop/notebook computer, wireless data port, smart phone, personal data assistant (PDA), tablet computing device, one or more processors within these devices, or any other suitable processing device, including physical or virtual instances (or both) of the computing device. Additionally, the computer 602 can comprise a computer that includes an input device, such as a keypad, keyboard, touch screen, or other device that can accept user information, and an output device that conveys information associated with the operation of the computer 602, including digital data, visual, or audio information (or a combination of information), or a graphical-type user interface (UI) (or GUI).

The computer 602 can serve in a role as a client, network component, a server, a database or other persistency, or any other component (or a combination of roles) of a computer system for performing the subject matter described in the instant disclosure. The illustrated computer 602 is communicably coupled with a network 630. In some implementations, one or more components of the computer 602 can be configured to operate within environments, including cloud-computing-based, local, global, or other environment (or a combination of environments).

At a high level, the computer 602 is an electronic computing device operable to receive, transmit, process, store, or manage data and information associated with the described subject matter. According to some implementations, the computer 602 can also include or be communicably coupled with an application server, e-mail server, web server, caching server, streaming data server, or other server (or a combination of servers).

The computer 602 can receive requests over network 630 from a client application (for example, executing on another computer 602) and respond to the received requests by processing the received requests using an appropriate software application(s). In addition, requests can also be sent to the computer 602 from internal users (for example, from a command console or by other appropriate access method), external or third-parties, other automated applications, as well as any other appropriate entities, individuals, systems, or computers.

Each of the components of the computer 602 can communicate using a system bus 603. In some implementations, any or all of the components of the computer 602, hardware or software (or a combination of both hardware and software), can interface with each other or the interface 604 (or a combination of both), over the system bus 603 using an application programming interface (API) 612 or a service layer 613 (or a combination of the API 612 and service layer 613). The API 612 can include specifications for routines, data structures, and object classes. The API 612 can be either computer-language independent or dependent and refer to a complete interface, a single function, or even a set of APIs. The service layer 613 provides software services to the computer 602 or other components (whether or not illustrated) that are communicably coupled to the computer 602. The functionality of the computer 602 can be accessible for all service consumers using this service layer. Software services, such as those provided by the service layer 613, provide reusable, defined functionalities through a defined interface. For example, the interface can be software written in JAVA, C++, or other suitable language providing data in extensible markup language (XML) format or other suitable format. While illustrated as an integrated component of the computer 602, alternative implementations can illustrate the API 612 or the service layer 613 as stand-alone components in relation to other components of the computer 602 or other components (whether or not illustrated) that are communicably coupled to the computer 602. Moreover, any or all parts of the API 612 or the service layer 613 can be implemented as child or sub-modules of another software module, enterprise application, or hardware module without departing from the scope of this disclosure.

The computer 602 includes an interface 604. Although illustrated as a single interface 604 in FIG. 6, two or more interfaces 604 can be used according to particular needs, desires, or particular implementations of the computer 602. The interface 604 is used by the computer 602 for communicating with other systems that are connected to the network 630 (whether illustrated or not) in a distributed environment. Generally, the interface 604 comprises logic encoded in software or hardware (or a combination of software and hardware) and is operable to communicate with the network 630. More specifically, the interface 604 can comprise software supporting one or more communication protocols associated with communications such that the network 630 or interface's hardware is operable to communicate physical signals within and outside of the illustrated computer 602.

The computer 602 includes a processor 605. Although illustrated as a single processor 605 in FIG. 6, two or more processors can be used according to particular needs, desires, or particular implementations of the computer 602. Generally, the processor 605 executes instructions and manipulates data to perform the operations of the computer 602 and any algorithms, methods, functions, processes, flows, and procedures as described in the instant disclosure. Example processors include central processing unit (CPU), graphic processing unit (GPU), microcontroller (MCU), and many integrated core (MIC).

The computer 602 also includes a database 606 that can hold data for the computer 602 or other components (or a combination of both) that can be connected to the network 630 (whether illustrated or not). For example, database 606 can be an in-memory, conventional, or other type of database storing data consistent with this disclosure. In some implementations, database 606 can be a combination of two or more different database types (for example, a hybrid in-memory and conventional database) according to particular needs, desires, or particular implementations of the computer 602 and the described functionality. Although illustrated as a single database 606 in FIG. 6, two or more databases (of the same or combination of types) can be used according to particular needs, desires, or particular implementations of the computer 602 and the described functionality. While database 606 is illustrated as an integral component of the computer 602, in alternative implementations, database 606 can be external to the computer 602.

The computer 602 also includes a memory 607 that can hold data for the computer 602 or other components (or a combination of both) that can be connected to the network 630 (whether illustrated or not). Memory 607 can store any data consistent with this disclosure. In some implementations, memory 607 can be a combination of two or more different types of memory (for example, a combination of semiconductor and magnetic storage) according to particular needs, desires, or particular implementations of the computer 602 and the described functionality. Although illustrated as a single memory 607 in FIG. 6, two or more memories 607 (of the same or combination of types) can be used according to particular needs, desires, or particular implementations of the computer 602 and the described functionality. While memory 607 is illustrated as an integral component of the computer 602, in alternative implementations, memory 607 can be external to the computer 602.

The application 608 is an algorithmic software engine providing functionality according to particular needs, desires, or particular implementations of the computer 602, particularly with respect to functionality described in this disclosure. For example, application 608 can serve as one or more components, modules, or applications. Further, although illustrated as a single application 608, the application 608 can be implemented as multiple applications 608 on the computer 602. In addition, although illustrated as integral to the computer 602, in alternative implementations, the application 608 can be external to the computer 602.

The computer 602 can also include a power supply 614. The power supply 614 can include a rechargeable or non-rechargeable battery that can be configured to be either user- or non-user-replaceable. In some implementations, the power supply 614 can include power-conversion or management circuits (including recharging, standby, or other power management functionality). In some implementations, the power-supply 614 can include a power plug to allow the computer 602 to be plugged into a wall socket or other power source to, for example, power the computer 602 or recharge a rechargeable battery.

There can be any number of computers 602 associated with, or external to, a computer system containing computer 602, each computer 602 communicating over network 630. Further, the term "client," "user," and other appropriate terminology can be used interchangeably, as appropriate, without departing from the scope of this disclosure. Moreover, this disclosure contemplates that many users can use one computer 602, or that one user can use multiple computers 602.

Described implementations of the subject matter can include one or more features, alone or in combination.

For example, in an implementation, a computer-implemented method, comprises, generating a training data set using negative flash calculations, training a first machine learning algorithm to identify a supercritical phase and a subcritical phase, training a second machine learning algorithm to identify a number of stable phases in the subcritical phase and training a third machine learning algorithm to determine a phase split of the subcritical phase that has more than one identified stable phase.

The foregoing and other described implementations can each, optionally, include one or more of the following features:

A first feature, combinable with any of the following features, wherein the training data set includes input data points and output data points, and the output data points are calculated using the negative flash calculations based on the input data points.

A second feature, combinable with any of the previous or following features, wherein the output data points include supercritical data points, subcritical single-phase data point, and subcritical two-phase data points.

A third feature, combinable with any of the previous or following features, wherein the first machine learning algorithm is a RVM algorithm.

A fourth feature, combinable with any of the previous or following features, wherein the first machine learning algorithm is trained by solving a classification problem.

A fifth feature, combinable with any of the previous or following features, wherein the second machine learning algorithm is a RVM algorithm.

A sixth feature, combinable with any of the previous or following features, wherein the second machine learning algorithm is trained by solving a multi-class classification problem.

A seventh feature, combinable with any of the previous or following features, wherein the third machine learning algorithm is an artificial neural network algorithm.

An eighth feature, combinable with any of the previous or following features, wherein determining the phase split includes determining a mole fraction and a molar composition for each of the more than one stable phase.

A ninth feature, combinable with any of the previous or following features, further comprises using the trained first machine learning algorithm, the second trained machine learning algorithm, and the third trained machine learning algorithm to calculate isothermal phase equilibria.

A tenth feature, combinable with any of the previous or following features, further comprises constructing one or more Jacobian matrices for reservoir simulation based on the calculated isothermal phase equilibria.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs, that is, one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal, for example, a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums. Configuring one or more computers means that the one or more computers have installed hardware, firmware, or software (or combinations of hardware, firmware, and software) so that when the software is executed by the one or more computers, particular computing operations are performed.

The term "real-time," "real time," "realtime," "real (fast) time (RFT)," "near(ly) real-time (NRT)," "quasi real-time," or similar terms (as understood by one of ordinary skill in the art), means that an action and a response are temporally proximate such that an individual perceives the action and the response occurring substantially simultaneously. For example, the time difference for a response to display (or for an initiation of a display) of data following the individual's action to access the data can be less than 1 ms, less than 1 sec., or less than 5 secs. While the requested data need not be displayed (or initiated for display) instantaneously, it is displayed (or initiated for display) without any intentional delay, taking into account processing limitations of a described computing system and time required to, for example, gather, accurately measure, analyze, process, store, or transmit the data.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be, or further include special purpose logic circuitry, for example, a CPU, an FPGA (field programmable gate array), or an ASIC (application-specific integrated circuit). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example LINUX, UNIX, WINDOWS, MAC OS, ANDROID, IOS, or any other suitable conventional operating system.

A computer program, which can also be referred to or described as a program, software, a software application, a module, a software module, a script, or code can be written in any form of programming language, including compiled or interpreted languages, or declarative or procedural languages, and it can be deployed in any form, including as a stand-alone program or as a module, component, subroutine, or other unit suitable for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network.

While portions of the programs illustrated in the various figures are shown as individual modules that implement the various features and functionality through various objects, methods, or other processes, the programs can instead include a number of sub-modules, third-party services, components, libraries, and such, as appropriate. Conversely, the features and functionality of various components can be combined into single components, as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on general or special purpose microprocessors, both, or any other kind of CPU. Generally, a CPU will receive instructions and data from and write to a memory. The essential elements of a computer are a CPU, for performing or executing instructions, and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable storage device, for example, a universal serial bus (USB) flash drive, to name just a few.

Computer-readable media (transitory or non-transitory, as appropriate) suitable for storing computer program instructions and data includes all forms of permanent/non-permanent or volatile/non-volatile memory, media and memory devices, including by way of example semiconductor memory devices, for example, random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices; magnetic devices, for example, tape, cartridges, cassettes, internal/removable disks; magneto-optical disks; and optical memory devices, for example, digital video disc (DVD), CD-ROM, DVD+/−R, DVD-RAM, DVD-ROM, HD-DVD, and BLURAY, and other optical memory technologies. The memory can store various objects or data, including caches, classes, frameworks, applications, modules, backup data, jobs, web pages, web page templates, data structures, database tables, repositories storing dynamic information, and any other appropriate information including any parameters, variables, algorithms, instructions, rules, constraints, or references. Additionally, the memory can include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, for example, a CRT (cathode ray tube), LCD (liquid crystal display), LED (Light Emitting Diode), or plasma monitor, for displaying information to the user and a keyboard and a pointing device, for example, a mouse, trackball, or trackpad by which the user can provide input to the computer. Input can also be provided to the computer using a touchscreen, such as a tablet computer surface with pressure sensitivity, a multi-touch screen using capacitive or electric sensing, or other type of touchscreen. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a Web browser through which a user can interact with an implementation of the subject matter described in this specification, or any combination of one or more such back-end, middleware, or front-end components. The components of the system can be interconnected by any form or medium of wireline or wireless digital data communication (or a combination of data communication), for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n or 802.20 (or a combination of 802.11x and 802.20 or other protocols consistent with this disclosure), all or a portion of the Internet, or any other communication system or systems at one or more locations (or a combination of communication networks). The network can communicate with, for example, Internet Protocol (IP) packets, Frame Relay frames, Asynchronous Transfer Mode (ATM) cells, voice, video, data, or other suitable information (or a combination of communication types) between network addresses.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what can be claimed, but rather as descriptions of features that can be specific to particular implementations of particular inventions. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features can be described as acting in certain combinations and even initially claimed as such, one or more features from a claimed combination can, in some cases, be excised from the combination, and the claimed combination can be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations can be considered optional), to achieve desirable results. In certain circumstances, multitasking or parallel processing (or a combination of multitasking and parallel processing) can be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain this disclosure. Other changes, substitutions, and alterations are also possible without departing from the spirit and scope of this disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

What is claimed is:

1. A computer-implemented method, comprising:
generating a training data set using negative flash calculations;
training, using the training data set, a first machine learning algorithm to identify a supercritical phase and a subcritical phase based on a tie-line length (t) of a ternary diagram of data under analysis, wherein a value of t equal to 0 is indicative of a supercritical phase and a value of t greater than 0 is indicative of a subcritical phase;
training, using the training data set, a second machine learning algorithm to identify a number of stable phases in the subcritical phase based on a fraction ($\beta$) of moles in a vapor phase relative to a total number of moles in the data under analysis, wherein a value of $\beta$ between 0 and 1 is indicative of more than one stable phase; and
training a third machine learning algorithm to determine a phase split of the subcritical phase that has more than one identified stable phase based on a mole fraction and a molar composition for each of the more than one stable phase.

2. The computer-implemented method of claim 1, wherein the training data set includes input data points and output data points, and the output data points are calculated using the negative flash calculations based on the input data points.

3. The computer-implemented method of claim 2, wherein the output data points include supercritical data points, subcritical single-phase data point, and subcritical two-phase data points.

4. The computer-implemented method of claim 1, wherein the first machine learning algorithm is a relevance vector machine (RVM) algorithm.

5. The computer-implemented method of claim 1, wherein the first machine learning algorithm is trained by solving a classification problem.

6. The computer-implemented method of claim 1, wherein the second machine learning algorithm is a RVM algorithm.

7. The computer-implemented method of claim 1, wherein the second machine learning algorithm is trained by solving a multi-class classification problem.

8. The computer-implemented method of claim 1, wherein the third machine learning algorithm is an artificial neural network algorithm.

9. The computer-implemented method of claim 1, further comprising using the trained first machine learning algorithm, the second trained machine learning algorithm, and the third trained machine learning algorithm to calculate isothermal phase equilibria.

10. The computer-implemented method of claim 9, further comprising constructing one or more Jacobian matrices for reservoir simulation based on the calculated isothermal phase equilibria.

11. A non-transitory, computer-readable medium storing one or more instructions executable by a computer system to perform operations comprising:
generating a training data set using negative flash calculations;
training, using the training data set, a first machine learning algorithm to identify a supercritical phase and a subcritical phase based on a tie-line length (t) of a ternary diagram of data under analysis, wherein a value of t equal to 0 is indicative of a supercritical phase and a value of t greater than 0 is indicative of a subcritical phase;
training, using the training data set, a second machine learning algorithm to identify a number of stable phases in the subcritical phase based on a fraction ($\beta$) of moles in a vapor phase relative to a total number of moles in the data under analysis, wherein a value of $\beta$ between 0 and 1 is indicative of more than one stable phase; and
training a third machine learning algorithm to determine a phase split of the subcritical phase that has more than one identified stable phase based on a mole fraction and a molar composition for each of the more than one stable phase.

12. The non-transitory, computer-readable medium of claim 11, wherein the output data points include supercritical data points, subcritical single-phase data point, and subcritical two-phase data points.

13. The non-transitory, computer-readable medium of claim 11, wherein the first machine learning algorithm is a relevance vector machine (RVM) algorithm, the second machine learning algorithm is a RVM algorithm, and a third machine learning algorithm is an artificial neural network algorithm.

14. The non-transitory, computer-readable medium of claim 11, further comprising using the trained first machine learning algorithm, the second trained machine learning algorithm, and the third trained machine learning algorithm to calculate isothermal phase equilibria.

15. A computer-implemented system, comprising:
one or more computers; and
one or more computer memory devices interoperably coupled with the one or more computers and having tangible, non-transitory, machine-readable media storing instructions that, when executed by the one or more computers, perform operations comprising:
generating a training data set using negative flash calculations;
training, using the training data set, a first machine learning algorithm to identify a supercritical phase and a subcritical phase based on a tie-line length (t) of a ternary diagram of data under analysis, wherein a value of t equal to 0 is indicative of a supercritical phase and a value of t greater than 0 is indicative of a subcritical phase;
training, using the training data set, a second machine learning algorithm to identify a number of stable phases in the subcritical phase based on a fraction ($\beta$) of moles in a vapor phase relative to a total number of moles in the data under analysis, wherein a value of $\beta$ between 0 and 1 is indicative of more than one stable phase; and
training a third machine learning algorithm to determine a phase split of the subcritical phase that has more than one identified stable phase based on a mole fraction and a molar composition for each of the more than one stable phase.

16. The computer-implemented system of claim 15, wherein the training data set includes input data points and output data points, and the output data points are calculated using the negative flash calculations based on the input data points, and wherein the output data points include supercritical data points, subcritical single-phase data point, and subcritical two-phase data points.

17. The computer-implemented system of claim 15, wherein the first machine learning algorithm is a relevance vector machine (RVM) algorithm, the second machine learning algorithm is a RVM algorithm, and a third machine learning algorithm is an artificial neural network algorithm.

* * * * *